US006172207B1

(12) United States Patent
Damhaut et al.

(10) Patent No.: US 6,172,207 B1
(45) Date of Patent: Jan. 9, 2001

(54) METHOD FOR SYNTHESIZING LABELLED COMPOUNDS

(75) Inventors: Philippe E. Damhaut, Chenee; Michel Monclus, Jurbise; John J. Van Namen, Geraardsbergen; Eric Mulleneers, Tubize; Jean-Luc E. Morelle, Brussels; Christian F. Lemaire, Alleur; Andre Luxen, Ocquier; Benjamin P. Lauricella, Ans, all of (BE)

(73) Assignees: Coincidence S. A., Angleur; Universite Libre de Bruxelles, Brussels; Universite de Liege, Liege, all of (BE)

( * ) Notice: Under 35 U.S.C. 154(b), the term of this patent shall be extended for 0 days.

(21) Appl. No.: 08/981,331

(22) PCT Filed: Apr. 30, 1997

(86) PCT No.: PCT/BE97/00056

§ 371 Date: Jul. 29, 1998

§ 102(e) Date: Jul. 29, 1998

(87) PCT Pub. No.: WO97/42203

PCT Pub. Date: Nov. 13, 1997

(30) Foreign Application Priority Data

May 2, 1996 (BE) .................................................. 9600388

(51) Int. Cl.$^7$ .............................. C07H 15/00; B01L 3/00
(52) U.S. Cl. .................. 536/18.4; 536/18.5; 536/122; 536/124; 424/1.1; 422/102; 422/103; 422/104; 422/159
(58) Field of Search .................. 536/18.4, 18.5, 536/122, 124; 424/1.1; 422/102, 103, 104, 159

(56) References Cited

U.S. PATENT DOCUMENTS

| | | | |
|---|---|---|---|
| 5,264,570 | * 11/1993 | Johnson et al. | ........................ 536/122 |
| 5,312,592 | 5/1994 | Andersson . | |
| 5,415,843 | 5/1995 | Andersson . | |
| 5,436,325 | * 7/1995 | Johnson et al. | ........................ 536/4.1 |

FOREIGN PATENT DOCUMENTS

| | | |
|---|---|---|
| 93306081 | 8/1993 | (EP) . |
| 0 588 480 A1 | 3/1994 | (EP) . |
| PCT/US94/02366 | 3/1994 | (WO) . |
| WO 94/21653 | 9/1994 | (WO) . |

OTHER PUBLICATIONS

Mulholland, "Simple Rapid Hydrolysis of Acetyl Protecting Groups iin the FDG Synthesis Using Cation Exhange Resins", Nuclear Med. Biol. vol. 22, No. 1, pp. 19–23.
Fuchtner et al., "Basis Hydrolysis of 2–[$^{18}$F] Fluoro–1,3,4, 6–tetra–o–acetyl–D–glucose in the Preparation of 2–[$^{18}$] Fluoro–2–deoxy–D–glucose", Appl. Radiat. Isot. vol. 47, No. 1, pp. 61–66, 1996.

A New Synthesis of 2–Deoxy–2–(18F) Fluoro–D–Galactose Using (18F) Flouride Ion—Haradahir, Maeda, Kai and Kojima—Journal of Labelled Compounds and Radiopharmaceuticals vol. XXV Sep. 10, 1987.

Efficient Stereospecific Synthesis of No–Carrier–Added 2–(18F)–Fluoro–2–Deoxy–D–Glucose Using Aminopolyether Supported Nucleophilic Substitution—K. Hamacher, H.H. Coenen, and G. Stocklin—The Journal of Nuclear Medicine vol. 27, No. 2, Feb. 1986.

New High–Yield Synthesis of 18F–Labelled 2–Deoxy–2–Fluoro–D–Glucose—Mirko Diksic and Dean Jolly—Int. J. Appl. Radiat. Isot. vol. 34, No. 6 pp. 893–896 1983.

Routine Production of 2–Deoxy–2–(18F)Fluoro–D–Glucose by Direct Nucleophilic Exchange on a Quaternary 4–Aminopyridinium Resin—Toorongian, Mulholland, Jewett, Bachelor, and Kilbourn—Nucl. Med. Biol. vol. 17 No. 3, pp. 273–279, 1990.

Synthesis of (2–2H)–5–Ethynyl–1–(β–D–Ribofuranosyl) Imidazole–4–Carboxamide and 5–Ethynyl–1–([5–3H] –β–D–Ribofuranosyl) Imidazole–4–Carboxamide (EICAR)—Minakawa, Matsuda, Xia, Wiebe and Knaus—Journal of Labelled Compounds and Radiopharmaceuticals—vol. XXXVIII, No. 9.

Stable, Isotopically Substituted Carbohydrates: An Improved Synthesis of (6–13C) Aldohexoses—King–Morris, and Bondo—Carbohydrate Research, 175 (1988) 49–58—Elsevier Science Publishers.

* cited by examiner

Primary Examiner—James O. Wilson
(74) Attorney, Agent, or Firm—Knobbe, Martens, Olson & Bear, LLP

(57) ABSTRACT

A process and a device for synthesizing labeled compounds. The process involves preparing a labeling agent, labeling a precursor with the labeling agent, where the precursor is a protected substrate, and deprotecting the labeled precursor to convert the labeled precursor to a labeled compound by passing the labeled precursor through a solid support in a column or a cartridge. The process may be used to convert labeled tetraacetylfluoroglucose (TAFg) to labeled fluorodeoxy-glucose (FDG) for use in nuclear medical imaging. The process is more rapid than conventional methods and is performed at room temperature rather than high temperature for conventional technology.

23 Claims, 1 Drawing Sheet

1

METHOD FOR SYNTHESIZING LABELLED COMPOUNDS

FIELD OF THE INVENTION

The invention relates to a new process for synthesising labelled compounds such as 2-[$^{18}$F]fluoro-2-deoxy-D-glucose, more commonly called fluoro-deoxy glucose or FDG.

The invention also relates to a device for synthesising said labelled compounds which relies on this process, making an automatic processing possible, including possibly a single use kit of materials.

BACKGROUND OF THE INVENTION

FDG is a tracer increasingly used in nuclear medical imaging. This molecule, labelled with the radionucleide $^{18}$F, behaves in a way similar to glucose in the first step of its metabolization in the human body and allows to map and quantify this fundamental mechanism. It is indicated for diagnosis of numerous diseases.

The most widely spread synthesis method is the so-called Hamacher method, described by Hamacher K., Coenen H. and Stöcklin G. in "Efficient Stereospecific Synthesis of No-carrier-added-2-[$^{18}$F]fluoro-2-deoxy-D-glucoso Using Aminopolyether Supported Nucleophilic Substitution", Journal of Nuclear Medicine 27, 235 (1986). Several variations of such method have been developed and are presently used in various Positron Emission Tomography (TEP) laboratories.

The synthesis is substantially based upon the following operating steps:

Preparation of the fluorinating agent in a first step, the $^{18}$F is activated through "activating" agents such as KRYPTOFIX™ (also called K2.2.2), a trademark used in connection with the compound 4, 7, 13, 16, 21, 24-hexaoxo-1, 10-diazabicyclo-[8.8.8]-hexacosane, so as to make it more reactive. In some publications, they are called "phase transfer agents". The radionucleide is produced beforehand, generally by irradiation of $^{18}$O enriched water with a proton beam originating from a particle accelerator, as F⁻ (for instance H$^{18}$F, in an aqueous solution).

Labelling of the precursor

The fluorinating agent, made totally anhydrous by additions of acetonitrile (CH$_3$CN) and dry evaporations, is put in presence of a labelling substrate (precursor), generally the 1,3,4,6-tetra-O-acetyl-2-trifluoromethanesulphonyl-β-D-mannopyranose (more commonly called "triflate") solubilized in acetonitrile. A substitution reaction then occurs, where the trifluoromethane sulphonate group of the substrate is replaced by the $^{18}$F atom, resulting in the formation of 2-[$^{18}$F]fluoro-1,3,4,6-tetra-O-acetyl-D-glucose (abbreviated in tetraacetylfluoroglucose or TAFg).

Pre-purification

The reagent residues, particularly the Kryptofix® K2.2.2, are removed by passing the solution through a C18 "Sep-Pak®" on which the TAFg remains trapped. This Sep-Pak® is then rinsed with 10 ml 0.1M HCl. The activity is then desorbed with 2 ml tetrahydrofuran (or THF) towards the reactor where the THF is totally evaporated away.

Deprotection namely hydrolysis

The precursor, namely the TAFg, is converted into FDG by removing its four acetyl groups: these acetyl groups are eliminated by an acid hydrolysis carried out in a hot aqueous solution (2 ml 1M HCl at about 130° C. during 15 min.)

Injectable formulation

The resulting FDG-containing solution is made injectable by passing it through an ion retarding column, which reduces its acidity, followed by alumina and C18 Sep-Pak®, which retain other impurities, and by a filter for sterility. It is made isotonic by adding an appropriate amount of NaCl. It is ready for quality control and others conditioning treatments prior to administration.

This procedure has, however, a number of drawbacks, the main ones of which are:

the duration of such a procedure is about fifty minutes, particularly because of the number of the successive heating and evaporating steps, resulting in a 30% loss of activity just because of the 110 minute half-life of $^{18}$F, the automation of this procedure requires a quite complicated equipment and makes more difficult the manufacture of a single use device.

A recent study performed by Mulholland G. Keith (Simple Rapid Hydrolysis of Acetyl Protecting Groups in the FDG Synthesis Using Cation Exchange Resins, Nucl. Med. Biol. Vol. 22, No 1, pp. 19–23 (1995)) relating to hydrolysis has shown that the 1M HCl acid could be replaced by a cationic resin with similar functionalities. The sulphonic acid resin (Dowex® 50) in the previously wetted H⁺ form, is placed in the hydrolysis reactor before starting synthesis. The tetraacetylfluoroglucose (TAFg) resulting from the previous steps of the synthesis, solubilised in ether, is introduced into the reactor on the resin. The ether is evaporated within a period of 3 to 5 minutes. The reactor is then heated at 100° C. for 8 to 10 minutes. During the last minute, 2 ml water are added onto the resin. The solution extracted from the reactor contains the FDG directly available with a pH of about 4 to 5.5.

Such method, which is not implemented in vivo as far as it is known, shows that the acid hydrolysis can be performed in a dry condition on a solid support. Its main interest is that purification through an ion retarding column is no more needed, since the acidity of the FDG solution obtained is very weak and lies within the injection limits.

However, this method does not save time with respect to the "conventional" hydrolysis method described by Hamacher. The elimination of one reagent (1M HCl) for the hydrolysis is compensated for by the addition of the the resin into the hydrolysis reactor, said resin having moreover to be conditioned before use. This method does not avoid the need for heating and evaporating the solvants.

Another recent study from F. Füchtner et al. (Basic Hydrolysis of 2-[$^{18}$F]fluoro-1,3,4,6-tetra-O-acetyl-D-glucose in the Preparation of 2-[$^{18}$F]fluoro-2-deoxy-D-glucose, Appl. Radiat. Isot., vol. 47, No. 1, pp. 61–66 (1996)) has shown that the hydrolysis, performed usually in acid media, can be performed in basic media much faster and at room temperature.

The solution resulting from the labelling step is dry evaporated, only leaving the TAFg (and other non volatile residues) on the walls of the labelling reactor. An aqueous NaOH solution (preferably 2 ml, 0.3M) is transferred into the unheated reactor. After 2 minutes, the TAFg is hydrolysed into FDG with a yield of about 80%. The main advantage of this process is the reaction rate: 2 minutes instead of 8 to 10 minutes for the acid hydrolysis.

However, in practice, the fact that the reaction can be performed at room temperature is not an advantage in a reactor device, since before (or during) the hydrolysis, it will anyway be necessary to include a heating device to evaporate the acetonitrile (or the ether) originating from the labelling step and which is present together with the TAFg.

AIMS OF THE INVENTION

The present invention aims to provide an improved process allowing to solve the problems and drawbacks above mentioned, and in particular aims to:

reduce the duration and the complexity of the synthesis, and simplify the device.

The process according to the invention aims in particular to simplify the procedure to make its automation easier and to reduce the time of synthesis to improve its yield, while maintaining, possibly improving, the chemical yield of the synthesis process.

Specific advantages of the process and the device according to the invention are mentioned hereafter, in reference to the description of various alternative embodiments of the present invention.

CHARACTERISTIC FEATURES OF THE INVENTION

Figure 1:
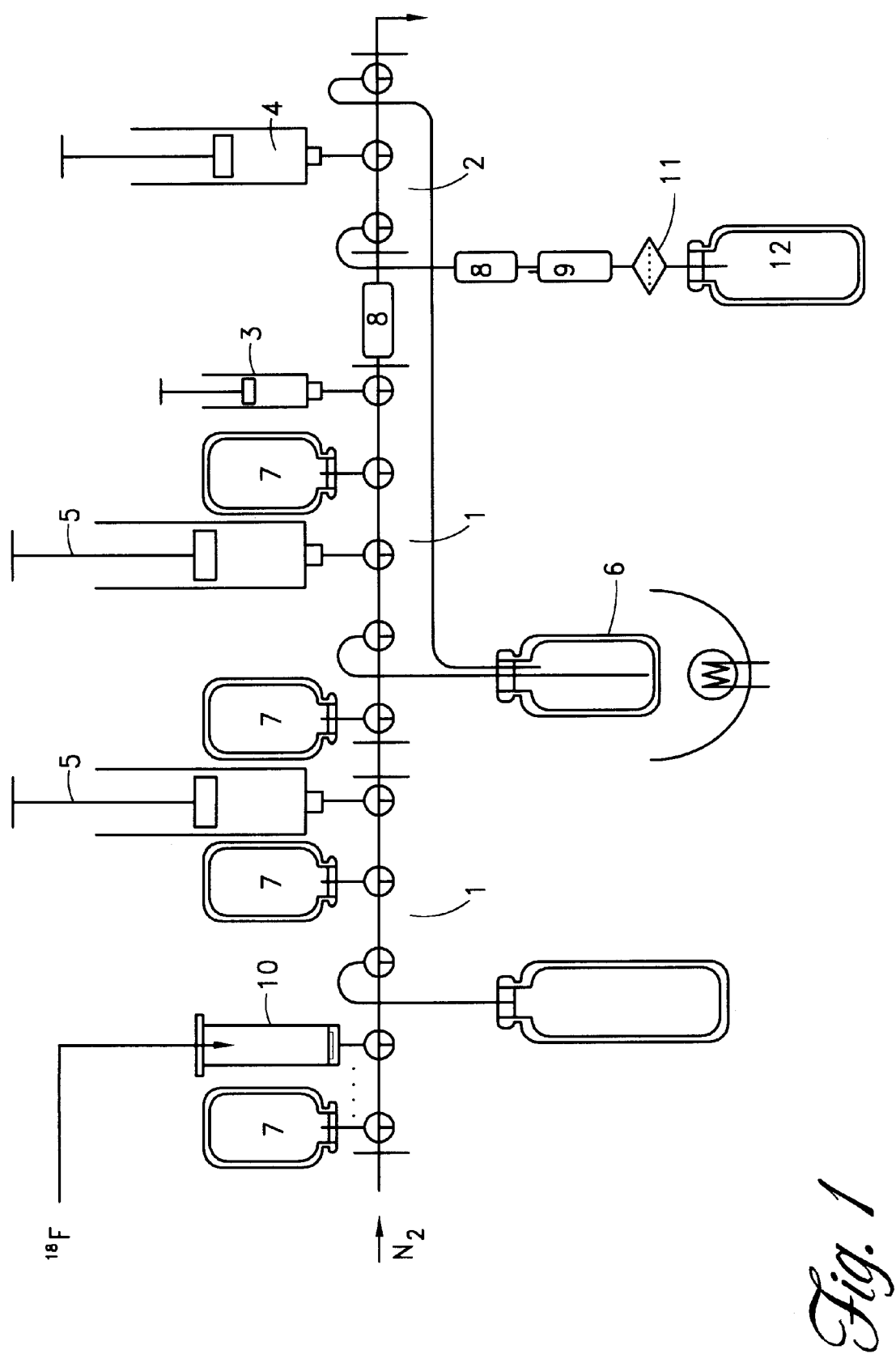
FIG. 1 is a schematic drawing illustrating the synthesis of 2-[$^{18}$F] fluoro-2-deoxy-D-glucose (FDG).

The process according to the invention relates to synthesis methods for labelled compounds with any isotopic element and used particularly in the medical field (NMR, therapy, medical imaging, . . . ), based upon the labelling of an organic substrate the functional groups of which are protected beforehand by protecting groups which, after the labelling step, can be easily removed by hydrolysis.

The process is characterised in that the elimination of said protecting groups in the deprotection step is obtained directly on a solid support comprised in a column or a cartridge, exhibiting a high affinity to the protected molecule and a low affinity to the deprotected molecule.

The term "functional groups" means functions such as alcohol, thiol, phenol, thiophenol, amines, ketones, aldehydes, carboxylic acids, etc.

The term "protecting groups" means groups (according to the function to be protected) such as acetyl, ethers, esters, thioesters, thioethers, imines, enamines, amides, carbamates, N-alkyles, N-aryles, N-hetero derivates, cetals, acetals, etc.

The term "column" or "cartridge" means any kind of stationary phase conditioning which may be used in chromatography, possibly including plastic or glass containers, columns, etc.

These products are commercially available and are in particular used in SPE (Solid Phase Extraction) applications and in solid phase chromatography.

According to a preferred embodiment of the present invention as applied to the synthesis of FDG according to the Hamacher method, the deprotection is performed directly on the column or cartridge of the solid support being used for the pre-purification or for the reformulation of the labelled precursor (elimination of the residual reagents and elimination of acetonitrile).

The cartridge used may be for example of the types C18, C8, tC18, NH2, diol, polystyrene divinylbenzene (SDB) or other polymeric phases, as for example available under the following trademarks:

Maxi-clean™ cartridges from Alltech:
C18, 300 mg cartridge (Alltech No. 20922)
C8, 300 mg cartridge (Alltech No. 20946)
NH2, 300 mg cartridge (Alltech No. 210040)
These cartridges also exist in 600 and 900 mg versions.
Waters cartridges, from 50 mg to 10 g, in particular:
C18 cartridges of Sep-Pak short body type (Waters No. WAT 020 515)
tC18 cartridges (trifunctional) of Sep-Pak short body type 400 mg (Waters No. WAT 036 810)
Waters OASIS HLB extraction cartridge.
Varian cartridges:
Microbond Elut C18 (re No. 1214-4002)
Microbond Elut C8 (re No. 1214-4405)
Microbond Elut PS-SDB (re No. 1214-4011)
Macherey-Nagel cartridges:
Chromabond C18 500 mg (re No. 730 003)
Chromabond Phenyl 500 mg (re No. 730 084)

The cartridges and columns being used contain between 50 mg and 10 g of a solid support. The preferred quantities are from 200 to 800 mg. Other quantities are also possible.

According to the invention, the solid support is of a normal, reverse or intermediate polarity phase type.

According to another preferred embodiment of the present invention, the solid support is of an ion exchange phase type or of a mixture of ion exchange phase type with one or several normal or reverse phases.

According to the invention, the solid support may be in the form of grains, membranes, sheets and/or capillaries.

For example, in the case of a de-acetylation as for the TAFg, the solid support is preferably of a low polarity.

Moreover, during the deprotecting step for the precursor, the solid support is advantageously impregnated with an agent enabling or increasing said deprotection. This deprotection agent may be an aqueous solution, preferably alkaline, or an acid aqueous solution.

According to another variation, the deprotection agent is the solid support itself.

Said alkaline aqueous solution is preferably an NaOH solution, and said aqueous acid solution is preferably an HCl solution. According to this embodiment, the solid support inside the column or cartridge in the deprotection step remains impregnated with the acid or alkaline solution between 1 and 5 minutes. Moreover, the preferred NaOH or HCl concentrations in the alkaline or acid solutions are comprised between 0.25 and 2M.

The labelled precursor is more efficiently trapped on the solid support in aqueous media or in auqeous media containing a small quantity of an organic solvent. Hence, the TAFg-acetonitrile solution (that results from the labelling step of the Hamacher method) is advantageously diluted with water in a proportion of 10 or more parts of water per 1 part of solvent. Other dilutions are also possible; dilutions from 5:1 and up allow a satisfactory fixing of the TAFg. It also appears that it can be advantageous to dilute the labelling solution with an acid solution, for example 0.1M HCl, to improve and simplify the efficiency of the prepurification when relevant, or with any other aqueous solution.

The mixture is transferred through the solid support column or cartridge and drained to the waste. The TAFg and some of its derivates, such as varieties of partially deacetylated TAFg, are retained on the support. Of course, the volume of the column or cartridge and the quantity of solid support it contains must be sufficient to retain most of the TAFg and its derivates.

The column or cartridge is then rinsed with an aqueous solution, either neutral or midly acid. These rinsing operations are performed so as to wash out the acetonitrile traces as well as some residues from the labelling step, present in the first transfer through the column or cartridge.

It should be noted that the rinsing step with the 0.1M HCl is optional: it depends upon the type of the reagents used in the labelling step or the composition of the extender added in the labelled solution before its transfer through the column of cartridge.

In its application to the synthesis of FDG and insofar a C18 type support is used, the procedure described so far conforms globally to the Hamacher method.

A NaOH solution is quickly (a few seconds) loaded into the column. The volume transferred is at least equal to the column content. The volume transferred to the column may exceed the column content and, in that case, the excess should be sent to the waste. The experience has shown that this excess only drains away a negligible amount of the useful compounds to the waste.

The solid support remains generally filled with NaOH during 1 to 5 minutes. Deprotection (hydrolysis) occurs during this period. Complete de-acetylation of the TAFg fixed on the solid support results in FDG, which has no affinity to the solid support, and is therefore found in the solution that impregnates the solid support. NaOH concentrations ranging from 0.2M to 2M have been successfully tested (the optimal concentration depending upon the support used). Other concentrations may be also considered, including zero concentration on some supports if hydrolysis can be spontaneous and fast, without any addition of NaOH, which would simplify considerably the subsequent purification.

The NaOH molarity of the solution and the column volume define together the total quantity of soda in the column or cartridge. Optimisation means here reducing this total quantity so as to make easier the subsequent neutralisation (or elimination) of the soda.

The period during which the column or cartridge must remain filled with the solution is the period required to obtain a virtually complete deprotection of the starting TAFg. It depends for example upon the molarity.

As an alternative to the use of an NaOH solution, an HCl solution may be loaded into the column instead and the deprotection may also be performed on the solid support in a similar way. It may be required to heat up the column or cartridge to carry out a complete hydrolysis.

The column or cartridge is then eluted with an eluent selected among the group consisting of water, an aqueous solution or a physiological solution. The FDG is carried by the solution. Said solution is transferred to the final vial through such elements as an ion retarding column, $Al_2O_3$ and C18 Sep-Pak® and a filter so as to purify and sterilize it. The elution may be carried out using an HCl solution to neutralise the NaOH (or the opposite in case of an acid hydrolysis). In such a case, the use of an ion retarding column is avoided. The pH adjustment and isotonicity to injectable standards of the final solution is performed adding a buffer. This buffer may be a solution of citrate or sodium phosphate, tris or any other injectable buffer.

The nature and size of the purification elements will notably depend upon the quantity of soda or acid used for the deprotection (hydrolysis).

The main advantages of the deprotection in a solid phase column or cartridge are the following:

from the labelling step onwards, no evaporation is anymore required;

no intermediate solvent is anymore used (ethanol in Hamacher method or ether in Mulholland method and in the process of the equipment manufacturers CTI or IBA) to perform the pre-purification;

the alkaline deprotection in a column or cartridge is quick and requires no heating;

no reactor is needed for the deprotection;

the total quantity of base (or acid) needed for deprotection is reduced to the column or cartridge volume. Its elimination is thereby simplified. Alternatively, its neutralisation is made possible by addition of a small quantity of acid (or base) and buffer;

the use of an ion retarding column is avoided.

The deprotection, by example by hydrolysis, within a solid support element, and in particular within the one used for pre-purification, allows to shorten the synthesis time, to reduce the number of reagents and to reduce the number of components of a device for producing labelled compounds. This simplification makes the process easier to implement in a automated synthesis device including a single use kit.

A last aspect of the present invention concerns the device for the synthesis of 2-[$^{18}$F]fluoro-2-deoxy-D-glucose (FDG) through the process of the invention, in which a solid support is used in the deprotection step, preferably included in a single use kit of materials.

Said device is advantageously automated.

DESCRIPTION OF A PREFERRED EMBODIMENT OF THE INVENTION

The invention will be described more in details, in reference to an example of a specific embodiment which is illustrated schematically in the enclosed FIG. 1.

EXAMPLE

Synthesis of 2-[$^{18}$F]fluoro-2-deoxy-D-glucose using multiple stopcock manifolds and disposible sterile syringes The synthesis of 2-[$^{18}$F]fluoro-2-deoxy-D-glucose (FDG) performed in the module illustrated in the enclosed schematic drawing (FIG. 1) includes the following steps:

recovery of the $^{18}$O enriched water, drying of the fluorinating agent [K/222]$^{+18}$ F$^-$, labelling of the triflate, pre-purification, deprotection (hydrolysis) on solid support in alkaline media, formulation of the injectable solution.

This process is carried out in a single use kit (FIG. 1) comprising the following single use components:

| Component | Trademark or supplier | Reference | Qty |
|---|---|---|---|
| 5-Stopcock-manifold (1) | PVB | 888-105 | 2 |
| 3-stopcock-manifold (2) | PVB | 888-103 | 1 |
| Syringe 2 ml (3) | Terumo | BS-02S | 1 |
| Syringe Plastipak 20 ml (4) | Becton-Dickinson | 300134 | 1 |
| Syringe Plastipak 60 ml (5) | Becton-Dickinson | 300856 | 2 |
| Reactor vial (6) | Alltech | 66124 | 1 |
| Reagent vial (7) | Alltech | 6655 | 4 |
| Tear-off seal | Alltech | 66440 | 1 |
| Septum | Alltech | 95313 | 1 |
| tC18 cartridge (8) | Waters | 36810 | 2 |
| Neutral alumina cartridge | Waters | 20510 | 1 |
| SAX cartridge, EMPORE (10) | Varian/3M | 1214-4023 | 1 |
| Filter 0.22 µm (11) | Millipore | SVGS0250S | 1 |

-continued

| Component | Trademark or supplier | Reference | Qty |
|---|---|---|---|
| Vacuum sterile vial (12) | Mallinckrodt | DRN4370 | 1 |
| Extension tube | Vygon | 110901 | 2 |
| Needle | B. Braun | 466 579/1 | 1 |

The abbreviation SAX refers to Strong Anion eXchange.

The following operating steps allow to obtain FDG by using the system above described. The synthesis reaction occurs as follows:

1. recovery of the [$^{18}$O] enriched water using an anionic resin,
2. recovery, by elution of the anionic resin, of the activity in the form of [K/222]$^{18+}$ F$^-$ in a solution in a mixture $CH_3CN/H_2O$,
3. evaporation of the solvent by IR heating (105° C.) under nitrogen flow (2 min. 30 sec.),
4. addition of 1 ml $CH_3CN$, evaporation (2 min. 30 sec.),
5. addition of 1 ml $CH_3CN$, evaporation to siccity (determination of the evaporation end through a temperature probe),
6. cooling of the reactor to 70° C.,
7. addition of a solution of a labelling precursor (15 mg) in $CH_3CN$ (1.7 ml),
8. heating at 95° C. during 3 min. (labelling step),
9. dilution of the resulting solution in 25 ml water,
10. transfer of the diluted solution through a C18 cartridge (conditioned beforehand with 5 ml ethanol followed with 10 ml water) to the waste,
11. rinsing of the cartridge with 10 ml 0.1 N HCl and 10 ml water which are sent to the waste,
12. drying of the cartridge under nitrogen flow,
13. addition of 0.7 ml 1.5M NaOH on the C18 cartridge,
14. deprotection (hydrolysis) 1.5 min. at room temperature,
15. elution of the FDG with 5 ml water into a syringe containing 0.8 ml 1.5M HCl and 5 ml of citrate buffer, and
16. transfer of the resulting solution through a C18 cartridge, a neutral alumina cartridge and a 0.22 µm filter; the solution is collected in a sterile vial.

What is claimed is:

1. A process for synthesizing labeled compounds with an isotopic element, comprising the steps of:
    preparing a labelling agent;
    labelling a precursor with the labelling agent, wherein the precursor is a protected substrate;
    pre-purifying the labelled precursor;
    retaining the labelled precursor on a solid support;
    deprotecting the labelled precursor, wherein deprotecting the labelled precursor converts the labelled precursor into a labelled compound in a deprotection step, wherein the labelled compound is free of the solid support; and
    formulating a final solution,
    wherein the deprotection step is performed directly on the solid support which is contained in a column or cartridge and wherein the labelled compound is 2-[$^{18}$F]fluoro-2-deoxy-D-glucose (FGD).

2. The process according to claim 1, wherein the column or cartridge is of a commercial type.

3. The process according to claim 1, wherein the deprotection step is performed directly in the solid support column or cartridge being used for pre-purification.

4. The process according to claim 1, wherein the solid support is of a normal, reverse or intermediate polarity phase type.

5. The process according to claim 1, wherein the solid support is of a low polarity.

6. The process according to claim 1, wherein the deprotection step is performed on a solid support of an ion exchange phase type or of a mixture of ion exchange phase type with one or several normal or reverse phases.

7. The process according to claim 1, wherein the deprotection step is performed on a column or cartridge selected from the group consisting of C18, C8, tC18, NH2, diol, and polystyrene divinylbenzene (SDB).

8. The process according to claim 1, wherein the cartridge or column contains between 50 mg and 10 g of a solid support.

9. The process according to claim 1, wherein the solid support is in the form of grains, membranes, sheets or capillaries.

10. The process according to claim 1, wherein, during the deprotection step, the solid support is impregnated with an agent enabling or increasing said deprotection.

11. The process according to claim 1, wherein the deprotection is performed by saponification.

12. The process according to claim 11, wherein said saponification is carried out with the help of an NaOH aqueous solution.

13. The process according to claim 1, wherein said deprotection is carried out by an acid hydrolysis.

14. The process according to claim 13, wherein said hydrolysis is carried out with an HCl aqueous solution.

15. The process according to claim 1, wherein the solid support contained in the column or cartridge during the deprotection step remains in acid or alkaline media for 1 to 5 minutes.

16. The process according to claim 15, wherein base or acid concentrations between 0.2 and 2M are used.

17. The process according to claim 1, wherein the deprotection agent is the solid support itself.

18. The process according to claim 1, wherein, after the deprotection step, the cartridge or column is eluted by an eluent selected from the group consisting of water, an aqueous solution, and a physiological solution, wherein said eluent drains the labelled compound with the solution and wherein the labelled compound is collected.

19. The process according to claim 1, wherein a solution of labelled precursor in acetonitrile is used and wherein said solution is diluted 5:1 with water or an aqueous solution.

20. The process according to claim 1, wherein the protected precursor is 1,3,4,6-tetra-O-acetyl-2-trifluoromethanesulphonyl-β-D-mannosepyranose (TAFg).

21. The process according to claim 8, wherein the cartridge or column contains between between 200 mg and 800 mg of a solid support.

22. The process according to claim 18, wherein the collected labelled compound is purified, filtered or sterilized.

23. The process according to claim 2, wherein said column or cartridge is implemented in a Solid Phase Extraction (SPE) technique.

* * * * *